United States Patent [19]

Umezawa et al.

[11] 4,401,594
[45] Aug. 30, 1983

[54] L-ARGININAL DERIVATIVES AND A METHOD OF MANUFACTURING THE SAME

[75] Inventors: Hamao Umezawa; Tomio Takeuchi, both of Tokyo; Takaaki Aoyagi, Fujisawa; Shinichi Ishii, Sapporo; Tetsushi Saino, Yono; Tetsuya Someno, Tokyo, all of Japan

[73] Assignee: Nippon Kayaku Kabushiki Kaisha, Tokyo, Japan

[21] Appl. No.: 300,443

[22] Filed: Sep. 8, 1981

[30] Foreign Application Priority Data

Sep. 19, 1980 [JP] Japan .............................. 55-129097

[51] Int. Cl.³ .......................................... C07C 103/52
[52] U.S. Cl. ............................................ 260/112.5 R
[58] Field of Search .................. 424/177; 260/112.5 R

[56] References Cited

U.S. PATENT DOCUMENTS 3,840,513 10/1974 Umezawa et al. ................. 424/177

OTHER PUBLICATIONS

Biol. Abstr., vol. 65, 35256 (1978).
Chem. Abstr., vol. 77, (1972) 165066d.
Chem. Abstr., vol. 83, (1975) 43760d.
Chem. Abstr. vol. 83, (1975) 10882s.

Chem. Abstr., vol. 76, (1972) 46521t.
Chem. Pharm. Bull. 23, (12) 3081-3087, 3106-3113 (1975).
Biochimica et Biophysica Acta 525, (1978) 429-437.

*Primary Examiner*—Delbert R. Phillips
*Attorney, Agent, or Firm*—Henry C. Nields

[57] ABSTRACT

L-Argininal derivatives of the general formula:

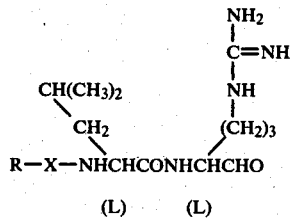

are disclosed.

A method of manufacturing any such derivative is also disclosed. The L-argininal derivative of this invention has a strong inhibitory activity on proteases, such as serine and thiol proteases, and is expected to provide useful medicines, including those which are effective for diseases caused by abnormal elevation of protease activity.

8 Claims, No Drawings

L-ARGININAL DERIVATIVES AND A METHOD OF MANUFACTURING THE SAME

BACKGROUND OF THE INVENTION

1. Field of the Invention:

This invention relates to L-argininal derivatives, and a method of manufacturing the same.

2. Description of the Prior Art:

It has already been ascertained by Umezawa, Aoyagi et al. that peptide derivatives containing aminoaldehydes (argininals) produced from certain kinds of actinomyces have a strong inhibitory activity on certain kinds of proteases, such as serine and thiol proteases. See, for example, H. Umezawa: The Journal of Antibiotics, 22, 1969, p. 283; or H. Umezawa: Enzyme Inhibitors of Microbial Origin, University of Tokyo Press, Tokyo, 1972, pp. 15-29.

Proteases in a living body not participate in blood coagulation, fibrinolysis or kinin release, but also act sometimes as inflammatory substances, and they play an inportant role on complement fixation, cell fusion, carcinogenesis, immunity, and various other phenomena. The inhibitors of the proteases, which are closely concerned in the various phenomena of life, are considered to have a lot of physiological actions, and are expected as useful medicines. In fact, it is known that leupeptin (acetyl or propionyl-L-leucyl-L-leucyl-L-argininal), which is a peptide containing argininal, has an antiinflammatory activity, and a pharmacological action on the fibrinolytic system. This compound has a potential therapeutic capability in muscular dystrophy, since it has recently been found that leupeptin inhibits the atrophy of the muscles in chickens with spontaneous muscular dystrophy [P. Libby and A. G. Stracher and E. B. MacGowan, Science, 200, p. 50 (1978)].

SUMMARY OF THE INVENTION

The L-argininal derivative of this invention is a compound obtained when the acetyl or propionyl-L-leucyl group in leupeptin is replaced by another substituent. It has a strong inhibitory activity on serine and thiol proteases, and is expected to provide useful medicines, for example, those which are effective for various diseases caused by the abnormal elevation of protease activity, such as acute or chronic pancreatitis, myocarbial infarction and muscular dystrophy.

DETAILED DESCRIPTION OF THE INVENTION

This invention provides L-argininal derivatives of the general formula I:

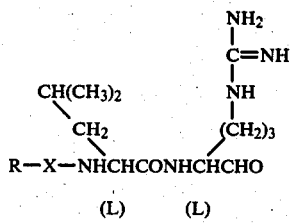

in which X is —CO— or —SO$_2$—, and R is (1) an alkyl group having 3 to 8 carbon atoms, a cycloalkyl group having 3 to 6 carbon atoms, or a pyridyl, benzyloxy, furyl or thiophene group, (2) a phenyl or benzyl group, which may be optionally substituted on the benzene ring by a halogen atom, or a lower alkyl or alkoxy, hydroxyl or nitro group, (3) a naphthyl group optionally substituted on the naphthalene ring by a lower alkylamino group, (4) a pyrrolidinyl, pyrrolidone or piperidyl group optionally having its nitrogen site protected by a benzyloxycarbonyl group, or (5) a group of the formula Z—Y—, in which Y is a hydroxymethylene or benzyloxycarbonylaminomethylene group, and Z is a lower alkyl, phenyl, benzyl, or α-benzyloxycarbonylamino-β-phenylethyl group, and a method of manufacturing them.

Typical examples of the compounds of this invention, which are represented by the formula I, include the following:

1. n-Butanoyl-L-leucyl-L-argininal hydrochloride;
2. 2-Ethylbutanoly-L-leucyl-L-argininal hydrochloride;
3. n-Hexanoly-L-leucyl-L-argininal hydrochloride;
4. 3-Methylbutanoyl-L-leucyl-L-argininal hydrochloride;
5. n-Nonanoyl-L-leucyl-L-argininal hydrochloride;
6. Cyclohexanecarbonyl-L-leucyl-L-argininal hydrochloride;
7. Cyclopropanecarbonyl-L-leucyl-L-argininal hydrochloride;
8. Benzoyl-L-leucyl-L-argininal hydrochloride;
9. m-Chlorobenzoyl-L-leucyl-L-argininal hydrochloride;
10. p-Methylbenzoyl-L-leucyl-L-argininal hydrochloride;
11. p-Methoxybenzoyl-L-leucyl-L-argininal hydrochloride;
12. p-Nitrobenzoyl-L-leucyl-L-argininal hydrochloride;
13. Benzenesulfonyl-L-leucyl-L-argininal hydrochloride;
14. p-Toluenesulfonyl-L-leucyl-L-argininal hydrochloride;
15. Phenylacetyl-L-leucyl-L-argininal hydrochloride;
16. o-Nitrophenylacetyl-L-leucyl-L-argininal hydrochloride;
17. p-Nitrophenylacetyl-L-leucyl-L-argininal hydrochloride;
18. o-Hydroxyphenylacetyl-L-leucyl-L-argininal hydrochloride;
19. 2-Naphthalenecarbonyl-L-leucyl-L-argininal hydrochloride;
20. 1-Naphthalenesulfonyl-L-leucyl-L-argininal hydrochloride;
21. 5-Dimethylamino-1-naphthalenesulfonyl-L-leucyl-L-argininal 2 hydrochloride;
22. Isonicotinyl-L-leucyl-L-argininal hydrochloride;
23. Nicotinyl-L-leucyl-L-argininal hydrochloride;
24. pyridine-2-carbonyl-L-leucyl-L-argininal hydrochloride;
25. Benzyloxycarbonyl-L-leucyl-L-argininal hydrochloride;
26. Furan-2-carbonyl-L-leucyl-L-argininal hydrochloride;
27. Thiophene-2-carbonyl-L-leucyl-L-argininal hydrochloride;
28. N-Benzyloxycarbonyl-L-prolyl-L-leucyl-L-argininal hydrochloride;
29. L-Prolyl-L-leucyl-L-argininal 2 hydrochloride;
30. N-Benzyloxycarbonyl-L-pyroglutamyl-L-leucyl-L-argininal hydrochloride;
31. L-Pyroglutamyl-L-leucyl-L-argininal hydrochloride;

32. N-Benzyloxycarbonyl-DL-pipecolyl-L-leucyl-L-argininal hydrochloride;
33. DL-Pipecolyl-L-leucyl-L-argininal 2 hydrochloride;
34. N-Benzyloxycarbonyl-L-leucyl-L-leucyl-L-argininal hydrochloride;
35. DL-Mandelyl-L-leucyl-L-argininal hydrochloride;
36. N-Benzyloxycarbonyl-L-phenylalanyl-L-leucyl-L-argininal hydrochloride; and
37. N-Benzyloxycarbonyl-(2S,3R)-3-amino-2-hydroxy-4-phenylbutanoyl-L-leucyl-L-argininal hydrochloride.

Compounds Nos. 1, 3, 5, 6, 8, 12, 14, 17, 18, 19, 21, 23, 30, 31, 34, 35, 36 and 37 are preferable, and compounds Nos. 1, 5, 17, 23, 30, 31 and 36 are most preferable.

The compound of this invention represented by the formula I, which is an optically active argininal derivative, is very difficult to manufacture by a purely synthetic process, since argininal per se is difficult to synthesize, and is very labile to racemization.

The inventors of this invention have made a extensive research for a method of manufacturing an optically active argininal derivative, and have consequently discovered that the compound of the formula I can be easily obtained if L-leucyl-L-argininal having a protected aldehyde group and obtained by an enzymatic degradation of leupeptin having a protected aldehyde group is employed as the starting material. This discovery has provided a basis for the present invention.

According to this invention, the aldehyde group may be protected as a lower dialkylacetal, such as dibutylacetal.

The compound of this invention can be manufactured when L-leucyl-L-algininal having a protected aldehyde group is reacted with an acylating or sulfonylating agent, and the protecting group is, then, removed from the aldehyde group. If there is any other protecting group, it may first be removed if required, before the protecting group of the aldehyde group is removed. The acylation or sulfonylation of the starting compound may be carried out by any method ordinarily employed in peptide chemistry, for example:
(1) A method employing an acid halide;
(2) A method employing an active ester, such as N-hydroxysuccinimide, p-nitrophenol or pentachlorophenol;
(3) A method employing a carbodiimide, such as dicyclohexylcarbodiimide or ethyldimethylaminopropylcarbodiimide;
(4) A method employing a condensing agent, such as diphenylphosphoryl azidate, N-ethoxycarbonyl-2-ethoxydihydroquinoline or N-ethyl-5-phenylisooxazolium-3'-sulfonate;
(5) A method employing a mixed acid anhydride, such as ethyl chloroformate or isobutyl chloroformate; or
(6) A method employing an azide.

If the acyl group is an aminoacyl group, any of the aforesaid amide-bond linking method may be applied after the functional group not participating in the reaction is protected by any protecting group ordinarily employed in peptide synthesis. If the acyl group is an alkyloxycarbonyl or aralkyloxycarbonyl group, it is possible to employ an acylating agent, such as alkyl (or aralkyl) oxycarbonyl chloride, or alkyl (or aralkyl) S-4,6-dimethylpyrimidine-2-ylthiolcarbonate.

The acylating or sulfonylating agent may be a compound of the general formula II:

$$R''-W \quad \text{(II)}$$

in which is a reactive derivative of —COOH or —SO$_3$H, and R'' is (1) an alkyl group having 3 to 8 carbon atoms, a cycloalkyl group having 3 to 6 carbon atoms, or a pyridyl, benzyloxy, furyl or thiophene group, (2) a phenyl or benzyl group optionally substituted on the benzene ring by a halogen atom, or a lower alkyl or alkoxy, hydroxyl or nitro group, (3) a naphthyl group optionally substituted on the naphthalene ring by a lower alkylamino group, (4) a pyrrolidinyl, pyrrolidone or piperidyl group having a nitrogen site protected by a benzyloxycarbonyl group, or (5) a group of the formula Z—Y— in which Y is a hydroxymethylene or benzyloxycarbonylaminomethylene group, and Z is a lower alkyl, phenyl, benzyl or α-benzyloxycarbonylamino-β-phenylethyl group.

Examples of the compounds represented by the formula II include reactive derivatives of saturated aliphatic or alicyclic carboxylic acids, such as n-butanoyl chloride, 2-ethyl-n-butanoyl chloride, 3-methyl-n-butanoyl chloride, n-hexanoyl chloride, n-nonanoyl chloride, cyclopropanecarboxylic acid, diphenylphosphoryl azidate, and cyclohexanecarboxylic acid N-hydroxysuccinimide ester; reactive derivatives of benzoic acids, such as benzoic acid diphenylphosphoryl azidate m-chlorobenzoic acid N-hydroxysuccinimide ester, p-toluic acid N-hydroxysuccinimide ester, p-methoxybenzoic acid N-hydroxysuccinimide ester, and p-nitrobenzoyl chloride; reactive derivatives of acetic acid, such as o-hydroxyphenylacetic acid N-hydroxysuccinimide ester, phenylacetic acid chloride, o-nitrophenylacetic acid N-hydroxysuccinimide ester, p-nitrophenylacetic acid N-hydroxysuccinimide ester, and phenylacetic acid N-hydroxysuccinimide ester; reactive derivatives of naphthalenecarboxylic acids, such as 2-naphthalenecarboxylic acid N-hydroxysuccinimide ester; reactive derivatives of amino acids, such as N-benzyloxycarbonyl-L-phenylalanine N-hydroxysuccinimide ester, N-benzyloxycarbonyl-(2S,3R)-3-amino-2-hydroxy-4-phenylbutanoic acid N-hydroxysuccinimide ester, N-benzyloxycarbonyl-L-pyroglutamic acid N-hydroxysuccinimide ester, N-benzyloxycarbonyl-L-proline N-hydroxysuccinimide ester, and N-benzyloxycarbonyl-L-leucine N-hydroxysuccinimide ester; reactive derivatives of mandelic acids, such as mandelic acid N-hydroxysuccinimide ester; reactive derivatives of pyridine-carboxylic acid, such as isonicotinic acid N-hydroxysuccinimide ester, nicotinic acid N-hydroxysuccinimide ester, and pyridine-2-carboxylic acid N-hydroxysuccinimide ester; reactive derivatives of pipecolic acids, such as N-benzyloxycarbonylpipecolic acid N-hydroxysuccinimide ester; reactive derivarive of thiophenecarboxylic acids, such as thiophene-2-carboxylic acid N-hydroxysuccinimide ester; reactive derivatives of furancarboxylic acids, such as furan-2-carboxylic acid N-hydroxysuccinimide ester; reactive derivatives of benzenesulfonic acids, such as p-toluenesulfonyl chloride and benzenesulfonyl chloride; reactive derivatives of naphthalenesulfonic acids, such as 5-dimethylamino-1-naphthalenesulfonyl chloride, and 1-naphthalenesulfonyl chloride; and benzyl S-4,6-dimethyl-pyrimidine-2-ylthiolcarbonate.

The compound acylated or sulfonylated as hereinabove described can be purified most easily and efficiently by silica gel column chromatography, since it is difficult to crystallize, as is the case with any other compound containing a guanidino group.

The leucylargininal derivative thus obtained may be subjected to hydrolysis, whereby the protecting group is removed from the aldehyde group. If the derivative is insoluble in water, it may be dissolved in a solvent miscible with water, such as methanol, ethanol, acetone, acetonitrile, dimethylformamide, tetrahydrofuran or dioxane, and the solution may be reacted with a mineral acid, such as hydrochloric or sulfuric acid, for several hours at room temperature. Although there is no particular limitation to the concentration of the acid, it is preferably in the range of 0.3 to 0.5 N. If the dialkylacetal derivative obtained is soluble in water, it may be hydrolyzed only in the aforesaid acid. After completion of the hydrolysis, the excess acid is removed by using a weakly basic ion exchange resin, for example, Dowex WGR ®, and the neutralized solution is freezed-dried to yield a salt of the intended compound.

If there exists any other protecting group than the one for the aldehyde group, it should be removed by, for example, catalytic reduction before the protecting group for the aldehyde group is removed.

The non-toxic salt of the L-argininal derivative thus obtained may, for example, be a pharmaceutically allowable organic acid such as acetic acid, lactic acid, succinic acid, fumaric acid, tartaric acid, benzoic acid, salicylic acid, methanesulfonic acid or toluenesulfonic acid, or an inorganic acid such as a mineral acid or phosphoric acid.

Typical compounds of this invention were tested for enzyme inhibitory activity on papain, trypsin, kallikrein and plasmin, which are typical examples of serine and thiol proteases.

DETERMINATION OF INHIBITORY ACTIVITY ON ENZYMES

The inhibitory activity of the compounds on each protease was determined as follows:

Determination of Anti-Papain Activity

Buffer solution: pH 7.4, 0.05 M borate buffer solution.

Substrate: To the solution of 2 g of casein (milk, Wako Junyaku Co., Osaka, Japan) in 90 ml of distilled water was added 1 N sodium hydroxide to adjust ph 7.4 under heating. Thus, 100 ml of a casein solution were prepared.

Enzyme: Papain (Green Cross Co., Japan) was dissolved in the buffer solution to form an enzyme solution having a papain concentration of 1 mg/ml, and the solution was kept in a cold and dark place. The enzyme solution was adjusted prior to use so that 0.1 ml thereof might show an absorbance of 0.4 at 280 nm after 20 minutes of reaction.

Method: 1.0 ml of the casein solution, 0.8 ml of the buffer solution, and 0.1 ml of the test sample or water were placed in a test tube (15 mm × 100 mm). After the solution in the test tube had been heated at 37° C. for three minutes, 0.1 ml of the enzyme solution was added into the solution in the test tube, and reacted therewith at 37° C. for 20 minutes. When the reaction had been completed, a 1.7 M solution of perchloric acid was added into the test tube, and the contents were shaken slightly. After the test tube had been stood at room temperature for an hour, its contents were centriguged at 3,000 rpm for 10 minutes. The absorbance (a) of the supernatant thus obtained was measured at 280 nm. The absorbance (b) of the controll solution not containing any compound of this invention was also measured.

Determination of Anti-Trypsin Activity

Buffer solution: pH 7.4, 0.05 M borate buffer solution.

Substrate: To the solution of 2 g of casein (milk, Wako Junyaku Co., Osaka, Japan) in 90 ml of distilled water was added 1 N sodium hydroxide to adjust pH 7.4 under heating. Thus, 100 ml of a casein solution were prepared.

Enzyme: Trypsin (Worthington Biochemical Co., U.S.A.) was dissolved in the fubber solution to form an enzyme solution having a trypsin concentration of 200 $\mu$g/ml, and the solution was kept in a cold and dark place. The enzyme solution was adjusted prior to use so that 0.1 ml thereof might show an absorbance of 0.4 at 280 nm after 20 minutes of reaction.

Method: 1.0 ml of the casein solution, 0.8 ml of the buffer solution, and 0.1 ml of the test sample or water were placed in a test tube (15 mm × 100 mm). After the solution in the test tube had been heated at 37° C. for three minutes 0.1 ml of the enzyme solution was added into the solution in the test tube, and reacted therewith at 37° C. for 20 minutes. When the reaction had been completed, a 1.7 M solution of perchloric acid was added into the test tube, and contents of the test tube were shaken slightly. After the test tube had been stood at room temperature for an hour, its contents were centrifuged at 3,000 rpm for 10 minutes. The absorbance (a) of the supernatant thus obtained was measured at 280 nm. The absorbance (b) of the controll olution not containing any compound of this invention was also measured.

Determination of Anti-kallikrein Activity

Buffer solution: ph 8.0, 0.05 M phsphate buffer solution.

Substrate: N-benzoly-L-arginine ethyl ester hydrochloride was dissolved in the buffer solution to form a 2 mM solution.

Enzyme: Kallikrein (Bayer, 1,080 KE/mg) was dissolved in the buffer solution to form a solution having a kallikrein concentration of 10 KE/ml. The enzyme solution was adjusted prior to use so that 0.03 ml thereof might show an absorbance of 0.4 at 253 nm after 20 minutes of reaction.

Method: 1.4 ml of the buffer solution, 0.5 ml of the substrate solution, and 0.07 ml of the test sample or water were placed in a test tube (15 mm × 100 mm). After the solution in the test tube had been left at room temperature for three minutes, 0.03 ml of the enzyme solution was added into the solution in the test tube, and reacted therewith at room temperature for 20 minutes. When the reaction had been completed, the absorbance (a) of the solution was measured at 253 nm immediately. The absorbance (b) of the controll solution not containing any compound of this invention was also measured.

Determination of Anti-Plasmin Activity

Buffer solution: pH 7.2, 0.01 M phosphate buffer solution.

Substrate: 2 g of fibrinogen (Armour Pharm. Co., U.S.A.) were dissolved in 100 ml of the phosphate buffer solution under heat.

Enzyme: The human serum was mixed with 20 times as much water, and after acetic acid had been added into the mixture to adjust it to pH 5.2, the solution was left at room temperature for half an hour. The precipitates obtained by centrifugation at 3,000 rpm for 10 minutes was dissolved in an equal quantity of the buffer solution to that of the serum, and the resulting solution was subjected to centrigugation at 10,000 rpm for half an hour, whereby a plasminogen solution was obtained as the supernatant. A solution of streptokinase (Varidase, Lederle Lab., U.S.A.) having a concentration of 10,000 U/ml was prepared, and kept in a cold and dark place. Prior to use, it was diluted with the buffer solution into a solution having a concentration of 2,000 U/ml. The enzyme solution was adjusted prior to use so that 0.5 ml thereof might show an absorbance of about 0.4 at 280 nm after 20 minutes of reaction.

Method: 0.5 ml of the plasminogen solution, 0.3 ml of the phosphate buffer solution, 0.1 ml of the streptokinase solution, and 0.1 ml of the test sample or water were placed in a test tube (15 mm × 100 mm). After the mixed solution in the test tube had been heated at 37° C. for three minutes, 2.0 ml of the fibrinogen solution were added into the solution in the test tube, and reacted therewith at 37° C. for 20 minutes. When the reaction had been completed, 1.5 ml of a 1.7 M perchloric acid solution were added into the test tube, and its contents were shaken slightly. After the test tube had been stood at room temperature for an hour, its contents were subjected to centrigugation at 3,000 rpm for 10 minutes. The absorbance (a) of the supernatant thus obtained was measured at 280 nm. The absorbance (b) of the controll solution not containing any compound of this invention was also measured.

The inhibition coefficients of the compounds of this invention on each enzyme were calculated from the absorbances (a) and (b) obtained as hereinabove described, in accordance with the following formula:

$$\frac{b - a}{b} \times 100$$

These inhibition rates were obtained for various concentrations of the compounds according to this invention, and the concentration of a 50% inhibition ($IC_{50}$) were calculated therefrom.

The following table shows the inhibitory activity of typical compounds of this invention on the enzymes:

TABLE

| Compound | $IC_{50}$ (mcg/ml) | | | |
|---|---|---|---|---|
| | Papain | Trypsin | Kallikrein | Plasmin |
| Leupeptin | 0.4 | 1.0 | 4.8 | 4.7 |
| Invention No. | | | | |
| 1 | 0.20 | 5.0 | 2.0 | 14.3 |
| 2 | 0.40 | 9.0 | 3.3 | 30.0 |
| 3 | 0.15 | 1.5 | 3.0 | 6.2 |
| 4 | 0.50 | 3.0 | 1.5 | 8.4 |
| 5 | 0.11 | 0.80 | 6.0 | 1.2 |
| 6 | 0.23 | 15.0 | 1.8 | 23.4 |
| 7 | 0.17 | 26.0 | 12.5 | — |
| 8 | 0.50 | 14.0 | 3.0 | 18.3 |
| 9 | 0.85 | 4.5 | 1.4 | 6.0 |
| 10 | 0.09 | 11.0 | 7.5 | 14.0 |
| 11 | 0.11 | 13.5 | 9.0 | 17.3 |
| 12 | 0.11 | 14.5 | 3.2 | 14.0 |
| 13 | 0.13 | 1.2 | 40.0 | 10.7 |
| 14 | 0.10 | 0.80 | 70.0 | 6.7 |
| 15 | 0.14 | 1.4 | 6.0 | 6.2 |
| 16 | 0.25 | 3.2 | 7.5 | 20.0 |
| 17 | 0.11 | 1.1 | 3.0 | 1.7 |
| 18 | 0.17 | 1.3 | 3.3 | 5.7 |
| 19 | 0.10 | 6.5 | 4.5 | — |
| 20 | 0.06 | 4.2 | — | 13.0 |
| 21 | 0.14 | 0.85 | 40.0 | 12.3 |
| 22 | 0.31 | 16.0 | 2.5 | 33.4 |
| 23 | 0.14 | 5.0 | 0.75 | 9.0 |
| 24 | 0.37 | 42.0 | 8.0 | — |
| 25 | 0.15 | 8.5 | 15.0 | 15.0 |

TABLE-continued

| Compound | $IC_{50}$ (mcg/ml) | | | |
|---|---|---|---|---|
| | Papain | Trypsin | Kallikrein | Plasmin |
| 26 | 0.14 | 27.0 | 8.5 | 36.3 |
| 27 | 0.20 | 40.0 | 11.0 | — |
| 28 | 0.11 | 6.0 | 7.5 | — |
| 29 | 0.60 | 10.0 | 0.4 | — |
| 30 | 0.17 | 0.15 | 14.0 | 0.53 |
| 31 | 0.75 | 0.50 | 1.1 | 0.50 |
| 32 | 0.33 | 6.5 | 18.0 | — |
| 33 | 5.0 | 5.5 | 0.18 | — |
| 34 | 0.15 | 0.8 | 7.3 | — |
| 35 | 0.30 | 0.70 | 14.0 | 1.4 |
| 36 | 0.40 | 0.80 | 1.0 | 0.73 |
| 37 | 0.70 | 0.70 | 3.3 | 1.4 |

As is obvious from the foregoing table, all of these novel compounds according to this invention have an outstanding degree of inhibitory activity on enzymes, and are, therefore, expected to provide useful medicines.

The invention will now be described more specifically with reference to examples. In the examples, the Rf values of the thin-layer chromatography were all obtained by using Merck 0.25 mm silica gel plates 60F254, and a developing solvent composed of n-butanol, butyl acetate, acetic acid and water with a mixing ratio of 4:2:1 (v/v). The measurement of the optical rotation was carried out by using a mercury lamp at 578 nm, and an acetic acid. The determination of the compounds was carried out by field desorption mass spectrometry.

EXAMPLE 1

Manufacture of Benzoyl-L-leucyl-L-argininal hydrochloride (Compound No. 8)

146 mg of benzoic acid, and 437 mg of L-leucyl-L-argininaldibutylacetal hydrochloride were dissolved in 5 ml of N,N'-dimethylformamide, and the resulting solution was cooled in an ice bath. Then, 215 mcl of diphenylphosphoryl azidate and 120 mcl of triethylamine were added into the solution, and the mixed solution thus obtained was stirred at room temperature for eight hours. The reaction mixture was concentrated to dryness, and subjected to silica gel chromatography with a developing solvent composed of n-butyl alcohol, n-butyl acetate, acetic acid and water with a mixing ratio of 4:2:1:1 (v/v). The fractions having the Rf value of 0.7, and showing a positive reaction for the Sakaguchi reagent and a negative reaction for the ninhydrin reagent were collected, and concentrated to dryness. The concentrated product was hydrolyzed at room temperature for 15 hours in a mixed solution containing one volume of 1 N hydrochloric acid and two volumes of acetonitrile. After 50 ml of water had been added into the reaction mixture, it was neutralized with a weakly basic ion exchange resin Dowex WGR ® (OH type). The resulting aqueous solution was freeze-dried to yeild 157 mg of Compound No. 8.

Rf*: 0.41 to 0.28;
$[\alpha]^{26}$ −13.9° (c=0.8).

*Referential Data: Rf of natural leupeptin: 0.41 to 0.28. Leupeptin gave three spots under the aforeside conditions of thin-layer chromatography.

EXAMPLE 2

Manufacture of DL-mandelyl-L-leucyl-L-argininal hydrochloride (Compound No. 35)

500 mg of DL-mandelic acid N-hydroxysuccinimide ester, and 437 mg of L-leucyl-L-argininaldibutylacetal hydrochloride were dissolved in 5 ml of N,N'-dimethylformamide while they were being cooled with ice. Then, 110 μl of N-methylmorpholine were added into the solution, and the solution was stirred for eight hours at room temperature. The reaction mixture was concentrated to dryness, and subjected to silica gel chromatography as in EXAMPLE 1. Likewise, the fractions having the Rf value of 0.7, and showing a positive reaction for the Sakaguchi reagent and a negative reaction for the ninhydrin reagent were collected, and concentrated to dryness. The procedures of EXAMPLE 1 for hydrolysis, neutralization and freeze drying were repeated to yield 169 mg of Compound No. 35.

Rf: 0.50 to 35;
$[\alpha]^{26}$ −63.2° (c=0.9).

EXAMPLE 3

Manufacture of p-toluenesulfonyl-L-leucyl-L-argininal hydrochloride (Compound No. 14)

191 mg of p-toluenesulfonyl chloride, and 437 mg of L-leucyl-L-argininaldibutylacetal hydrochloride were dissolved in 5 ml of chloroform while they were being cooled with ice. Then, 140 μl of triethylamine were added into solution, and the resulting solution was stirred for eight hours at room temperature. After the reaction mixture had been concentrated, the procedures of EXAMPLE 1 were repeated for silica gel chromatography, collection of the fractions having the Rf value of 0.7, and showing a positive reaction for the Sakaguchi reagent and a negative reaction for the ninhydrin reagent, concentration, and further treatment, whereby 140 mg of Compound No. 14 were obtained.

Rf: 0.54 to 0.40;
$[\alpha]^{30}$ −35.6° (c=1.2).

EXAMPLE 4

Manufacture of n-butanoly-L-leucyl-L-argininal hydrochloride (Compound No. 1)

The procedures of EXAMPLE 3 were repeated, except for the use of 107 mg of n-butanoyl chloride and 350 mg of L-leucyl-L-argininaldibutylacetal hydrochloride, whereby 212 mg of Compound No. 1 were obtained.

Rf: 0.51 to 0.33;
$[\alpha]^{26}$ −44.2° (c=1.4).

EXAMPLE 5

Manufacture of 2-ethyl-n-butanoyl-L-leucyl-L-argininal hydrochloride (Compound No. 2)

The procedures of EXAMPLE 3 were repeated, except for the use of 162 mg of 2-ethyl-n-butanoyl chlorode and 437 mg of L-leucyl-L-argininaldibutylacetal hydrochloride. There were obtained 250 mg of Compound No. 2.

Rf: 0.53 to 0.40;
$[\alpha]^{27}$ −55.5° (c=1.4).

EXAMPLE 6

Manufacture of n-hexanoyl-L-argininal hydrochloride (Compound No. 3)

The procedures of EXAMPLE 3 were repeated, except for the use of 135 mg of n-hexanoyl chloride and 350 mg of L-leucyl-L-argininaldibutylacetal hydrochloride. There were obtained 230 mg of Compound No. 3.

Rf: 0.56 to 0.40;
$[\alpha]^{27}$ −42.5° (c=1.1).

EXAMPLE 7

Manufacture of 3-methylbutanoyl-L-leucyl-L-argininal hydrochloride (Compound No. 4)

The procedures of EXAMPLE 3 were repeated, except for the use of 121 mg of 3-methylbutanoyl chloride and 350 mg of L-leucyl-L-argininaldibutylacetal hydrochloride. There were obtained 160 mg of Compound No. 4.

Rf: 0.51 to 0.37;
$[\alpha]^{26}$ −38.6° (c=0.9).

EXAMPLE 8

Manufacture of n-nonanoyl-L-leucyl-L-argininal hydrochloride (Compound No. 5)

The procedures of EXAMPLE 3 were repeated, except for the use of 176 mg of n-nonanoyl chloride and 350 mg of L-leucyl-L-argininaldibutylacetal hydrochloride. There were obtained 202 mg of Compound No. 5.

Rf: 0.64 to 0.46;
$[\alpha]^{27}$ −37.8° (c=1.1).

EXAMPLE 9

Manufacture of cyclohexanecarbonyl-L-leucyl-L-argininal hydrochloride (Compound No. 6)

The procedures of EXAMPLE 2 were repeated, except for the use of 448 mg of cyclohexanecarboxylic acid N-hydroxysuccinimide ester, and 437 mg of L-leucyl-L-argininal hydrochloride. There were obtained 180 mg of Compound No. 6.

Rf: 0.54 to 0.40;
$[\alpha]^{22}$ −45.1° (c=0.9).

EXAMPLE 10

Manufacture of cyclopropanecarbonyl-L-leucyl-L-argininal hydrochloride (Compound No. 7)

The procedures of EXAMPLE 1 were repeated, except for the use of 138 mg of cyclopropanecarboxylic acid, and 350 mg of L-leucyl-L-argininaldibutylacetal hydrochloride. There were obtained 97 mg of Compound No. 7.

Rf: 0.48 to 0.34;
$[\alpha]^{27}$ −47.1° (c=0.9).

EXAMPLE 11

Manufacture of o-hydroxyphenylacetyl-L-leucyl-L-argininal hydrochloride (Compound No. 18)

The procedures of EXAMPLE 2 were repeated, except for the use of 448 mg of o-hydroxyphenylacetic acid N-hydroxysuccinimide ester, and 350 mg of L-leucyl-L-argininaldibutylacetal hydrochloride. There were obtained 133 mg of Compound No. 18.

Rf: 0.55 to 0.39;
[α]$^{27}$ −41.3° (c=1.1).

EXAMPLE 12

Manufacture of m-chlorobenzyl-L-leucyl-L-argininal hydrochloride (Compound No. 9)

The procedures of EXAMPLE 2 were repeated, except for the use of 405 mg of m-chlorobenzoic acid N-hydroxysuccinimide ester, and 350 mg of L-leucyl-L-argininaldibutylacetal hydrochloride. There were obtained 119 mg of Compound No. 9.
Rf: 0.61 to 0.46;
[α]$^{27}$ −4.6° (c=1.6).

EXAMPLE 13

Manufacture of p-methylbenzoyl-L-leucyl-L-argininal hydrochloride (Compound No. 10)

The procedures of EXAMPLE 2 were repeated, except for the use of 233 mg of p-toluic acid N-hydroxysuccinimide ester, and 350 mg of L-leucyl-L-argininaldibutylacetal hydrochloride. There were obtained 130 mg of Compound No. 10.
Rf: 0.56 to 0.43;
[α]$^{27}$ −1.6° (c=0.5).

EXAMPLE 14

Manufacture of p-methoxybenzoyl-L-leucyl-L-argininal hydrochloride (Compound No. 11)

The procedures of EXAMPLE 2 were repeated, except for the use of 243 mg of p-methoxybenzoic acid N-hydroxysuccinimide ester, and 350 mg of L-leucyl-L-argininaldibutylacetal hydrochloride. There were obtained 166 mg of Compound No. 11.
Rf: 0.51 to 0.37;
[α]$^{27}$ +3.2° (c=1.1).

EXAMPLE 15

Manufacture of isonicotinyl-L-leucyl-L-argininal hydrochloride (Compound No. 22)

The procedures of EXAMPLE 2 were repeated, except for the use of 396 mg of isonicotinic acid N-hydroxysuccinimide ester, and 350 mg of L-leucyl-L-argininaldibutylacetal hydrochloride. There were obtained 140 mg of Compound No. 22.
Rf: 0.30 to 0.20;
[α]$^{28}$ −7.3° (c=0.6).

EXAMPLE 16

Manufacture of nicotinyl-L-leucyl-L-argininal hydrochloride (Compound No. 23)

The procedures of EXAMPLE 2 were repeated, except for the use of 400 mg of nicotinic acid N-hydroxysuccinimide ester, and 437 mg of L-leucyl-L-argininaldibutylacetal hydrochloride. There were obtained 179 mg of Compound No. 23.
Rf: 0.40 to 0.19;
[α]$^{30}$ −14.0° (c=1.4).

EXAMPLE 17

Manufacture of p-nitrobenzoyl-L-leucyl-L-argininal hydrochloride (Compound No. 12)

The procedures of EXAMPLE 3 were repeated, except for the use of 185 mg of p-nitrobenzoyl chloride, and 350 mg of L-leucyl-L-argininaldibutylacetal hydrochloride. There were obtained 145 mg of Compound No. 12.
Rf: 0.58 to 0.45;
[α]$^{27}$ +6.7° (c=1.5)

EXAMPLE 18

Manufacture of furan-2-carbonyl-L-leucyl-L-argininal hydrochloride (Compound No. 26)

The procedures of Example 2 were repeated, except for the use of 209 mg of furan-2-carboxylic acid N-hydroxysuccinimide ester, and 350 mg of L-leucyl-L-argininaldibutylacetal hydrochloride. There were obtained 140 mg of Compound No. 26.
Rf: 0.51 to 0.33;
[α]$^{28}$ −1.1° (c=1.4).

EXAMPLE 19

Manufacture of benzyloxycarbonyl-L-leucyl-L-argininal hydrochloride (Compound No. 25)

The procedures of EXAMPLE 3 were repeated, except for the use of 274 mg of benzyl S-4,6-dimethylpyrimidine-2-ylthiolcarbonate, and 350 mg of L-leucyl-L-argininaldibutylacetal hydrochloride. There were obtained 198 mg of Compound No. 25.
Rf: 0.58 to 0.44;
[α]$^{26}$ −14.4° (c=1.2).

EXAMPLE 20

Manufacture of benzenesulfonyl-L-leucyl-L-argininal hydrochloride (Compound No. 13)

The procedures of EXAMPLE 3 were repeated, except for the use of 212 mg of benzenesulfonic acid chloride, and 437 mg of L-leucyl-L-argininaldibutylacetal hydrochloride. There were obtained 106 mg of Compound No. 13.
Rf: 0.55 to 0.39;
[α]$^{27}$ −30.7° (c=0.5).

EXAMPLE 21

Manufacture of 5-dimethylamino-1-naphthalenesulfonyl-L-leucyl-L-argininal 2 hydrochloride (Compound No. 21)

The procedures of EXAMPLE 3 were repeated, except for the use of 276 mg of 5-dimethylamino-1-naphthalenesulfonyl chloride, and 350 mg of L-leucyl-L-argininaldibutylacetal hydrochloride. There were obtained 188 mg of Compound No. 21.
Rf: 0.57 to 0.43;
[α]$^{28}$ +20.9° (c=0.9).

EXAMPLE 22

Manufacture of B 1-naphthalenesulfonyl-L-leucyl-L-argininal hydrochloride (Compound No. 20)

The procedures of EXAMPLE 1 were repeated, except for the use of 227 mg of 1-naphthalenesulfonyl chloride, and 350 mg of L-leucyl-L-argininaldibutylacetal hydrochloride. There were obtained 156 mg of Compound No. 20.
Rf: 0.58 to 0.44;
[α]$^{26}$ −62.6° (c=1.2).

EXAMPLE 23

Manufacture of phenylacetyl-L-leucyl-L-argininal hydrochloride (Compound No. 15)

The procedures of EXAMPLE 3 were repeated, except for the use of 185 mg of phenylacetyl chloride, and 437 mg of L-leucyl-L-argininaldibutylacetal hydrochloride. There were obtained 131 mg of Compound No. 15.

Rf: 0.55 to 0.38;
$[\alpha]^{28}$ −42.7° (c=1.0).

EXAMPLE 24

Manufacture of o-nitrophenylacetyl-L-leucyl-L-argininal hydrochloride (Compound No. 16)

The procedures of EXAMPLE 2 were repeated, except for the use of 360 mg of o-nitrophenylacetic acid N-hydroxysuccinimide ester, and 350 mg of L-leucyl-L-argininaldibutylacetal hydrochloride. There were obtained 285 mg of Compound No. 16.

Rf: 0.47 to 0.32;
$[\alpha]^{26}$ −31.8° (c=1.8).

EXAMPLE 25

Manufacture of p-nitrophenylacetyl-L-leucyl-L-argininal hydrochloride (Compound No. 17)

The procedures of EXAMPLE 2 were repeated, except for the use of 360 mg of p-nitrophenylacetic acid N-hydroxysuccinimide ester, and 350 mg of L-leucyl-L-argininaldibutylacetal hydrochloride. There were obtained 176 mg of Compound No. 17.

Rf: 0.54 to 0.39;
$[\alpha]^{25}$ −30.1° (c=1.6).

EXAMPLE 26

Manufacture of N-benzyloxycarbonyl-L-phenylalanyl-L-leucyl-L-argininal hydrochloride (Compound No. 36)

The procedures of EXAMPLE 2 were repeated, except for the use of 712 mg of N-benzyloxycarbonyl-L-phenylalanine N-hydroxysuccinimide ester, and 360 mg of L-leucyl-L-argininaldibutylacetal hydrochloride. There were obtained 177 mg of Compound No. 36.

Rf: 0.67 to 0.51;
$[\alpha]^{26}$ −24.7° (c=0.8).

EXAMPLE 27

Manufacture of N-benzyloxycarbonyl-(2S,3R)-3-amino-2-hydroxy-4-phenylbutanoyl-L-leucyl-L-argininal hydrochloride (Compound No. 37)

The procedures of EXAMPLE 2 were repeated, except for the use of 450 mg of N-benzyloxycarbonyl-(2S,3R)-3-amino-2-hydroxy-4-phenylbutanoic acid N-hydroxysuccinimide ester, and 437 mg of L-leucyl-L-argininaldibutylacetal hydrochloride. There were obtained 130 mg of Compound No. 37.

Rf: 0.58 to 0.39;
$[\alpha]^{27}$ −17.2° (C=0.9).

EXAMPLE 28

Manufacture of N-benzyloxycarbonyl-L-pyroglutamyl-L-leucyl-L-argininal hydrochloride (Compound No. 30)

The procedures of EXAMPLE 2 were repeated, except for the use of 720 mg of N-benzyloxycarbonyl-L-pyroglutamic acid N-hydroxysuccinimide ester, and 437 mg of L-leucyl-L-argininaldibutylacetal hydrochloride. There were obtained 165 mg of Compound No. 30.

Re: 0.36 to 0.20;
$[\alpha]^{27}$ −46.3° (c=1.1).

EXAMPLE 29

Manufacture of L-pyroglutamyl-L-leucyl-L-argininal hydrochloride (Compound No. 31)

The succinimide ester, and dibutylacetal hydrochloride as employed in EXAMPLE 28 were reacted with each other in accordance with the method of EXAMPLE 2 to form N-benzyloxycarbonyl-L-pyroglutamyl-L-leucyl-L-argininalbibutylacetal hydrochloride. Then, 105 mg of the product were dissolved in 10 ml of methanol, and the resulting solution was subjected to catalytic reduction on palladium black for two hours. When the reaction had been completed, the palladium black was removed by filtration from the reaction product. After the filtrate had been concentrated to dryness, it was treated as described in EXAMPLE 1, whereby there obtained 74 mg of Compound No. 31.

Rf: 0.28 to 0.13;
$[\alpha]^{26}$ −48.6° (c=1.1).

EXAMPLE 30

Manufacture of N-benzyloxycarbonyl-L-prolyl-L-leucyl-L-argininal hydrochloride (Compound No. 28)

The procedures of EXAMPLE 2 were repeated, except for the use of 300 mg of N-benzyloxycarbonyl-L-proline N-hydroxysuccinimide ester, and 437 mg of L-leucyl-L-argininaldibutylacetal hydrochloride. There were obtained 230 mg of Compound No. 28.

Rf: 0.43 to 0.30;
$[\alpha]^{27}$ −76.0° (c=0.7).

EXAMPLE 31

Manufacture of L-prolyl-L-leucyl-L-argininal 2 hydrochloride (Compound No. 29)

The succinimide ester, and dibutylacetal hydrochloride as employed in EXAMPLE 30 were reacted with each other in accordance with the method of EXAMPLE 2 to form N-benzyloxycarbonyl-L-prolyl-L-leucyl-L-argininaldibutylacetal hydrochloride. Then, 100 mg of the product were treated as described in EXAMPLE 29 to yield 70 mg of Compound No. 29.

Rf: 0.10 to 0.01;
$[\alpha]^{27}$ −51.3° (c=0.9).

EXAMPLE 32

Manufacture of N-benzyloxycarbonyl-L-leucyl-L-leucyl-L-argininal hydrochloride (Compound No. 34)

The procedures of EXAMPLE 2 were repeated, except for the use of 360 mg of N-benzyloxycarbonyl-L-leucine N-hydroxysuccinimide ester, and 350 mg of L-leucyl-L-argininaldibutylacetal hydrochloride. There were obtained 180 mg of Compound No. 34.

Rf: 0.56 to 0.47;
[α]$^{27}$ −37.9° (c=0.8).

EXAMPLE 33

Manufacture of 2-naphthalenecarbonyl-L-leucyl-L-argininal hydrochloride (Compound No. 19)

The procedures of EXAMPLE 2 were repeated, except for the use of 269 mg of 2-naphthalenecarboxylic acid N-hydroxysuccinimide ester, and 350 mg of L-leucyl-L-argininaldibutylacetal hydrochloride. There were obtained 180 mg of Compound No. 19.
Rf: 0.53 to 0.42;
[α]$^{26}$ +24.2° C. (c=1.0).

EXAMPLE 34

Manufacture of Pyridine-2-carbonyl-L-leucyl-L-argininal hydrochloride (Compound No. 24)

The procedures of EXAMPLE 2 were repeated, except for the use of 220 mg of pyridine-2-carboxylic acid N-hydroxysuccinimide ester, and 350 mg of L-leucyl-L-argininaldibutylacetal hydrochloride. There were obtained 210 mg of Compound No. 24.
Rf: 0.37 to 0.29;
[α]$^{26}$ −5.4° (c=0.9).

EXAMPLE 35

Manufacture of N-benzyloxycarbonyl-DL-pipecolyl-L-leucyl-L-argininal hydrochloride (Compound No. 32)

The procedures of EXAMPLE 2 were repeated, except for the use of 346 mg of N-benzyloxycarbonyl-DL-pipecolic acid N-hydroxysuccinimide ester, and 350 mg of L-leucyl-L-argininaldibutylacetal hydrochloride. There were obtained 135 mg of Compound No. 32.
Rf: 0.53 to 0.44;
[α]$^{27}$ −40.0° (c=0.5).

EXAMPLE 36

Manufacture of DL-pipecolyl-L-leucyl-L-argininal 2 hydrochloride (Compound No. 33)

The succinimide ester, and dibutylacetal hydrochloride as employed in EXAMPLE 35 were reacted with each other in accordance with the procedures of EXAMPLE 2 to form N-benzyloxycarbonyl-DL-pipecolyl-L-leucyl-L-argininaldibutylacetal hydrochloride. Then, 92 mg of the product were treated as described in EXAMPLE 29 to yield 53 mg of powder of Compound No. 33.
Rf: 0.99 to 0.02;
[α]$^{26}$ −36.2° (c=0.7).

EXAMPLE 37

Manufacture of thiophene-2-carbonyl-L-leucyl-L-arginalhydrochloride (Compound No. 27)

The procedures of EXAMPLE 2 were repeated, except for the use of 225 mg of thiophene-2carboxylic acid N-hydroxysuccinimide ester, and 350 mg of L-leucyl-L-argininaldibutylacetal hydrochloride. There were obtained 143 mg of Compound No. 27.

Rf: 0.47 to 0.39;
[α]$^{32}$ −18.5° (c=1.6).

REFERENTIAL EXAMPLE

Manufacture of L-leucyl-L-argininaldibutylacetal hydrochloride 50 g of leupeptin hydrochloride, and 5 g of p-toluenesulfonic acid were suspended in 500 ml of n-butanol and 1,000 ml of benzene, and the suspension was refluxed for six hours. After the solvent had been removed under reduced pressure, 1,000 ml of ethyl acetate were added to the residue, and it was washed with a 10% sodium chloride solution. After the ethyl acetate layer had been dried over magnesium sulfate, the solvent was removed to afford 27.6 g of leupeptindibutylacetal. 36 g of leupeptindibutylacetal obtained by repeating the aforesaid procedures, and 1.8 g of thermolysin were suspended in 18 l of a 0.1 M N-ethylmorpholine hydrochlorid acid buffer solution containing 0.02 M calcium chloride having a pH value of 8.0. The suspension was subjected to incubation at 38° C. for 72 hrs. The reaction product was extracted twice with 1.2 l of n-butanol, and the extracts were combined and concentrated under reduced pressure. The oily substance thus obtained was subjected to silica gel column chromatography, and developed with a developing solvent composed of n-butanol, n-butyl acetate, acetic acid and water with a mixing ratio of 4:2:1:1 (v/v). The fractions having the Rf value of 0.27, and showing a positive reaction for both the Sakaguchi and ninhydrin reagents were collected to yield the intended compound.
Yield: 12.6 g.
Molecular ions: 401.

What is claimed is:
1. An L-argininal derivative of the general formula:

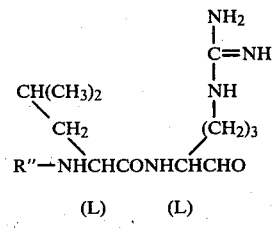

in which R" is a group selected from the group consisting of n-nonanoyl, m-chlorbenzoyl, p-methylbenzoyl, p-methoxybenzoyl, p-nitrobenzoyl, benzenesulfonyl, 2-naphthalenecarbonyl, 1-naphthalenesulfonyl, mandelyl, p-nitrophenylacetyl, L-nicotinyl, N-benzyloxycarbonyl-L-phenylalanyl, N-benzyloxycarbonyl-3-amino-2-hydroxy-4-phenylbutanoyl, N-benzyloxycarbonyl-L-prolyl, L-prolyl, N-benzyloxycarbonylpyroglutamyl, L-pyroglutamyl, p-toluenesulfonyl, and pipecolyl.

2. n-Nonanoyl-L-leucyl-L-argininal.
3. p-Nitrophenylacetyl-L-leucyl-L-argininal.
4. Nicotinyl-L-leucyl-L-argininal.
5. N-Benzyloxycarbonyl-L-phenylalanyl-L-leucyl-L-argininal.
6. N-Benzyloxycarbonyl-L-pyroglutamyl-L-leucyl-L-leucyl-L-argininal.
7. L-Pyroglutamyl-L-leucyl-L-argininal.
8. 5-Dimethylamino-1-naphthalenesulfonyl-L-leucyl-L-argininal.

* * * * *